US012364414B2

(12) United States Patent
Inoue

(10) Patent No.: US 12,364,414 B2
(45) Date of Patent: Jul. 22, 2025

(54) SLEEP POSITION DETERMINATION DEVICE USING CONTACTLESS SENSOR, SLEEP POSITION DETERMINATION METHOD, AND NON-TRANSITORY COMPUTER-READABLE RECORDING MEDIUM STORING PROGRAM FOR DETERMINING SLEEP POSITION

(71) Applicant: Panasonic Intellectual Property Management Co., Ltd., Osaka (JP)

(72) Inventor: Kenichi Inoue, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 1127 days.

(21) Appl. No.: 17/000,427

(22) Filed: Aug. 24, 2020

(65) Prior Publication Data
US 2020/0383611 A1 Dec. 10, 2020

Related U.S. Application Data

(63) Continuation of application No. PCT/JP2019/018314, filed on May 8, 2019.

(30) Foreign Application Priority Data

May 30, 2018 (JP) ................................ 2018-104098
Mar. 5, 2019 (JP) ................................ 2019-039710

(51) Int. Cl.
*A61B 5/11* (2006.01)
*A61B 5/00* (2006.01)
(Continued)

(52) U.S. Cl.
CPC .......... *A61B 5/1116* (2013.01); *A61B 5/0507* (2013.01); *A61B 5/08* (2013.01);
(Continued)

(58) Field of Classification Search
CPC ....... A61B 5/1116; A61B 5/0507; A61B 5/08; A61B 5/0816; A61B 5/113; A61B 5/4806;
(Continued)

(56) References Cited

U.S. PATENT DOCUMENTS 6,280,392 B1  8/2001  Yoshimi et al.
9,028,405 B2 * 5/2015  Tran ...................... A61B 5/411
                                                        600/300

(Continued)

FOREIGN PATENT DOCUMENTS

JP  2001-070256      3/2001
JP  2007-097996 A    4/2007
(Continued)

OTHER PUBLICATIONS

International Search Report of PCT application No. PCT/JP2019/018314 dated Jul. 16, 2019.
(Continued)

*Primary Examiner* — Matthew Kremer
*Assistant Examiner* — Jonathan M Haney
(74) *Attorney, Agent, or Firm* — GREENBLUM & BERNSTEIN, P.L.C.

(57) ABSTRACT

A sleep position determination device according to an embodiment of the present disclosure is provided with a receiver that receives a measurement result obtained by measuring a subject using a contactless sensor, an extraction circuit that extracts a respiration signal of the subject from the measurement result, memory that stores reference information related to a level of the respiration signal, and a determination circuit that determines a sleep position of the subject on a basis of a comparison between the level of the respiration signal of the subject and the reference information.

11 Claims, 17 Drawing Sheets

(51) Int. Cl.
    *A61B 5/0507*     (2021.01)
    *A61B 5/08*     (2006.01)
    *A61B 5/113*     (2006.01)
    *G01S 7/41*     (2006.01)
    *G01S 13/524*     (2006.01)

(52) U.S. Cl.
    CPC ............ *A61B 5/0816* (2013.01); *A61B 5/113* (2013.01); *A61B 5/4806* (2013.01); *A61B 5/746* (2013.01); *G01S 7/415* (2013.01); *G01S 13/524* (2013.01); *A61B 2503/04* (2013.01)

(58) Field of Classification Search
    CPC ... A61B 5/746; A61B 2503/04; A61B 5/1107; A61B 5/1114; A61B 5/1118; A61B 5/0826; G01S 7/415; G01S 13/524
    See application file for complete search history.

(56) References Cited

U.S. PATENT DOCUMENTS

| | | | | |
|---|---|---|---|---|
| 2006/0173257 | A1* | 8/2006 | Nagai | ................ A61B 5/14551 600/323 |
| 2009/0119843 | A1* | 5/2009 | Rodgers | ................. G16Z 99/00 705/3 |
| 2011/0295083 | A1* | 12/2011 | Doelling | ................. A61B 5/11 600/407 |
| 2014/0323823 | A1* | 10/2014 | Iskander | .............. A61B 5/0507 600/301 |
| 2016/0310046 | A1* | 10/2016 | Heinrich | .............. A61B 5/4818 |
| 2016/0328533 | A1* | 11/2016 | Kawai | ................. A61B 5/7405 |

FOREIGN PATENT DOCUMENTS

| | | |
|---|---|---|
| JP | 2012-005745 A | 1/2012 |
| JP | 2014-207934 A | 11/2014 |
| JP | 2014-207935 | 11/2014 |
| WO | 2016/136400 | 9/2016 |

OTHER PUBLICATIONS

English Translation of Chinese Search Report issued by the China National Intellectual Property Administration (CNIPA) in Chinese Patent Application No. 201980010881.6, dated Dec. 11, 2023.
English Translation of Chinese Search Report dated May 20, 2024 for the related Chinese Patent Application No. 201980010881.6.

* cited by examiner

| RANGE BIN | REFLECTION INTENSITY | PHASE ROTATION AMOUNT |
|---|---|---|
| 1 | $i_1$ | $r_1$ |
| 2 | $i_2$ | $r_2$ |
| 3 | $i_3$ | $r_3$ |
| ⋮ | ⋮ | ⋮ |
| n | $i_n$ | $r_n$ |

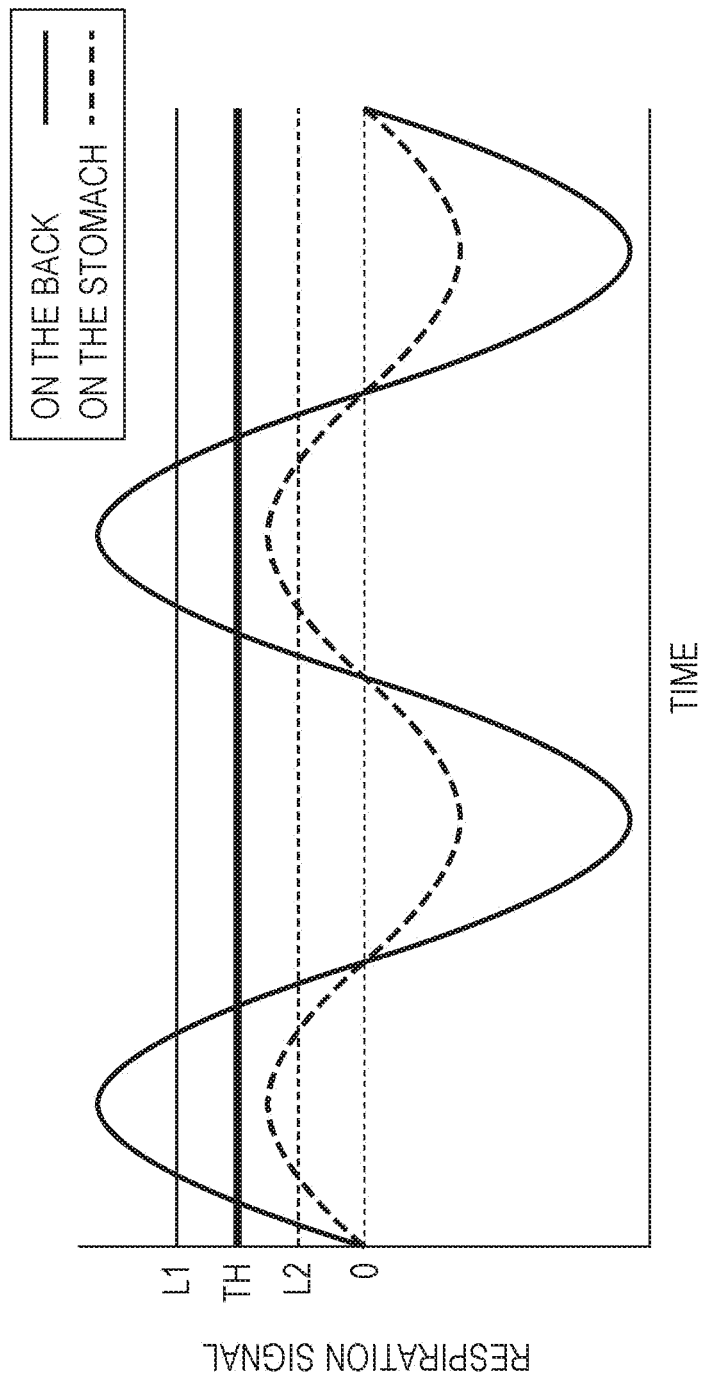

SLEEP POSITION DETERMINATION DEVICE USING CONTACTLESS SENSOR, SLEEP POSITION DETERMINATION METHOD, AND NON-TRANSITORY COMPUTER-READABLE RECORDING MEDIUM STORING PROGRAM FOR DETERMINING SLEEP POSITION

BACKGROUND

1. Technical Field

The present disclosure relates to a sleep position determination device using a contactless sensor, a sleep position determination method, and a non-transitory computer-readable recording medium storing a program for determining sleep position.

2. Description of the Related Art

There is a syndrome called sudden infant death syndrome (SIDS) in which an infant dies suddenly during sleep. Not putting infants to sleep on the stomach is known to be effective at reducing the risk of onset of SIDS. For example, in a nursery, the risk of SIDS is reduced by having a childcare worker periodically monitor an infant while the infant is taking a nap.

As an example of a technology that mechanically determines the sleep position of a subject, Japanese Unexamined Patent Application Publication No. 2001-070256 discloses a biomonitor system that computes the respiration signal, the sleep posture, and the bodyweight of a sleeping person on the basis of a plurality of load signals output by pressure-sensitive elements installed in a predetermined distribution underneath, inside, or on the surface of bedding.

SUMMARY

One non-limiting and exemplary embodiment provides a sleep position determination device, a sleep position determination method, and a non-transitory computer-readable recording medium storing program for determining sleep position with excellent ease of use.

In one general aspect, the techniques disclosed here feature a sleep position determination device provided with a receiver that receives, from at least one contactless sensor, a measurement result obtained by measuring a subject using the at least one contactless sensor, an extraction circuit that extracts a respiration signal of the subject from the measurement result, memory that stores first reference information related to a level of the respiration signal, and a determination circuit that determines a sleep position of the subject on a basis of a first comparison between the level of the respiration signal of the subject and the first reference information, and outputs a determination result of the sleep position.

According to the sleep position determination device of the present disclosure, by utilizing the property that the level of the respiration signal is different depending on the sleep position of the subject, it is possible to determine the sleep position of a subject on the basis of a comparison between the level of a respiration signal and reference information.

It should be noted that general or specific embodiments of the present disclosure may be implemented as a system, a method, an integrated circuit, a computer program, a computer-readable recording medium such as a CD-ROM disc, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 is a graph illustrating an example of respiration signals according to sleep positions according to Embodiment 1;

Figure 1:
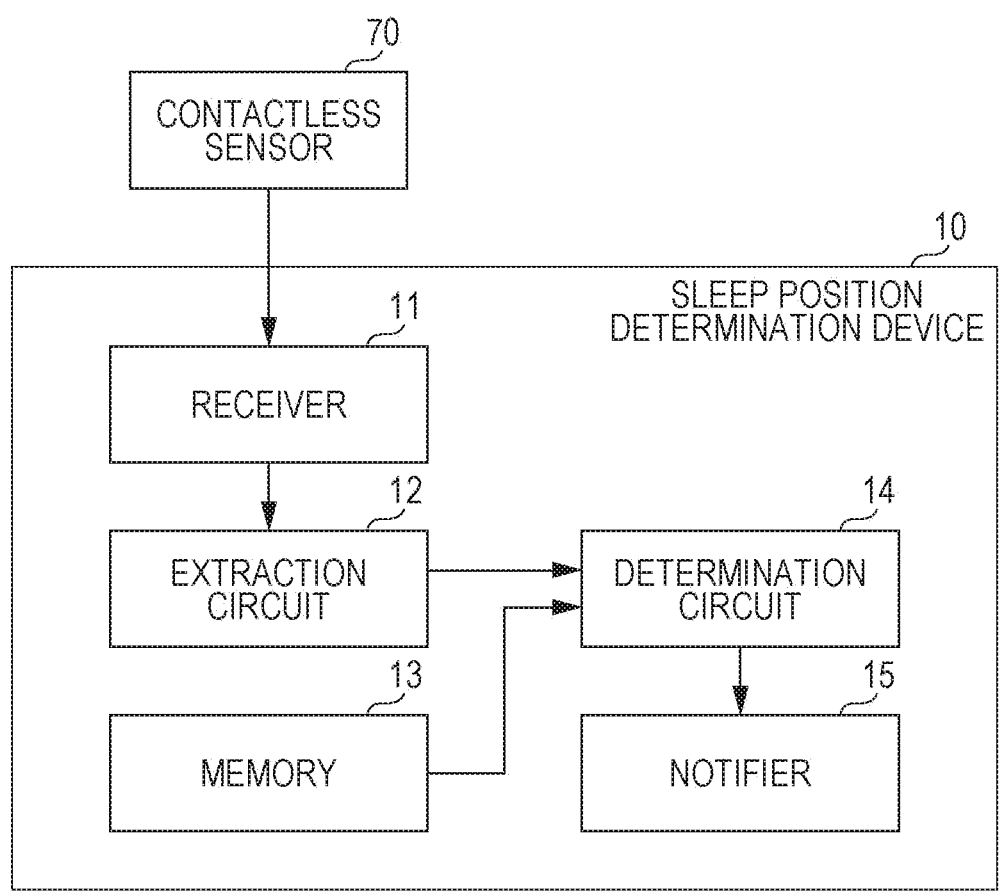
FIG. 1 is a block diagram illustrating an example of a functional configuration of a sleep position determination device according to Embodiment 1.

DETAILED DESCRIPTION (Underlying Knowledge Forming Basis of the Present Disclosure)

In the biomonitor system according to Japanese Unexamined Patent Application Publication No. 2001-070256, pressure-sensitive elements are installed in a predetermined distribution underneath, inside, or on the surface of bedding, and therefore the pressure-sensitive elements contact the subject directly or through the bedding. For this reason, in the case of using the biomonitor system according to Japanese Unexamined Patent Application Publication No. 2001-070256 to monitor the sleep position of an infant in a nursery, the comfort of the subject may be impaired, and furthermore, a large burden is imposed on the childcare workers and staff because of work such as replacing the pressure-sensitive elements due to wear and tear as well as daily disinfection.

If contactless sensors such as radar using radio waves and sonar using ultrasonic waves are used, it is possible to measure the position and motion of a subject in a contactless manner, but an effective technology that determines the sleep position of a subject from a measurement result from such contactless sensors has not been disclosed in the related art.

The inventor has discovered that the level of a respiration signal extracted from the measurement result of a contactless sensor is different depending on the sleep position of the subject. On the basis of this finding, the inventor proposes a sleep position determination device, a sleep position determination method, a non-transitory computer-readable recording medium, and a program that determine the sleep position of a subject from a measurement result obtained by measuring the subject with a contactless sensor.

A sleep position determination device according to an aspect of the present disclosure is provided with a receiver that receives, from at least one contactless sensor, a measurement result obtained by measuring a subject using the at least one contactless sensor, an extraction circuit that extracts a respiration signal of the subject from the measurement result, memory that stores first reference information related to a level of the respiration signal, and a determination circuit that determines a sleep position of the subject on a basis of a first comparison between the level of the respiration signal of the subject and the first reference information, and outputs a determination result of the sleep position.

According to such a configuration, by utilizing the property that the level of the respiration signal is different depending on the sleep position of the subject, it is possible to determine the sleep position of a subject on the basis of a comparison between the level of the extracted respiration signal and the first reference information. Because the respiration signal is extracted from the measurement result of the subject with a contactless sensor, compared to the case of using a contact sensor, the comfort of the subject is not impaired, and furthermore, the burden imposed on a user because of work such as replacing a pressure-sensitive element due to wear and tear as well as daily disinfection can be reduced. As a result, a sleep position determination device with excellent ease of use is obtained.

Also, the extraction circuit may extract a periodic body motion of the subject expressed by the measurement result as the respiration signal.

According to such a configuration, the respiration signal of the subject can be extracted from a time series of measurement results easily using specific methods such as a low-pass filter and a trend removal filter.

Also, the first reference information may be a threshold value of the level of the respiration signal. In a case where the level of the respiration signal of the subject is equal to or greater than the threshold value, the determination circuit may determine that the sleep position of the subject is on the back, and in a case where the level of the respiration signal of the subject is less than the threshold value, the determination circuit may determine that the sleep position of the subject is other than on the back.

According to such a configuration, by utilizing the property that the level of the respiration signal when the subject is sleeping on the back is higher than the level of respiration signal when the subject is sleeping in a sleep position other than on the back, the sleep position of the subject can be determined according to a comparison with the threshold value of the extracted respiration signal.

The sleep position determination device may be further provided with an update circuit that generates new first reference information using the respiration signal of the subject extracted in a case where the sleep position of the subject is determined to be on the back, and updates the first reference information stored in the memory with the new first reference information.

According to such a configuration, because the first reference information is updated according to the level of the respiration signal and the time variation of the level of the respiration signal specific to the subject, the sleep position of the subject can be determined precisely and consistently.

The sleep position determination device may be further provided with a rotation detector that detects a rotational movement of the subject from the measurement result, and the determination circuit may determine the sleep position of the subject on a basis of the first comparison and a detection result of the rotational movement.

According to such a configuration, the sleep position of the subject can be determined more accurately by recognizing whether or not a change in the sleep position, such as rolling over, has occurred in the subject through the detection of a rotational movement. This arrangement makes it possible to distinguish from a change of sleep position and detect a situation in which the subject is at risk of an abnormality, such as a cessation of breathing, in cases such as when the level of the respiration signal is lowered without being associated with a rotational movement.

Also, the at least one contactless sensor may include a plurality of contactless sensors, the plurality of contactless sensors may be provided in mutually different directions with respect to the subject, the receiver may receive the measurement result from each of the plurality of contactless sensors, the extraction circuit may extract a respiration signal of the subject from the measurement result for each of the plurality of contactless sensors, the memory may additionally store second reference information related to a relationship among levels of the respiration signals from the plurality of contactless sensors, and the determination circuit may determine the sleep position of the subject on a basis of a second comparison between the relationship among the levels of the respiration signals of the subject from the plurality of contactless sensors and the second reference information.

According to such a configuration, by utilizing the property that the relationship among the levels of respiration signals from a plurality of contactless sensors is different depending on the sleep position of the subject, it is possible to determine the sleep position of the subject more accurately on the basis of a comparison between the relationship among the levels of extracted respiration signals from a plurality of contactless sensors and second reference information.

Also, the second reference information may express a relationship among the levels of the respiration signals from the plurality of contactless sensors in correspondence with each of a plurality of sleep positions including on the back, on the side, and on the stomach, and the determination circuit may determine which among the plurality of sleep positions is the sleep position of the subject on the basis of the second comparison.

In such a configuration, the levels of the respiration signals extracted from the measurement results of the contactless sensors directly above and obliquely above the subject indicate a specific magnitude relationship in each of a plurality of sleep positions of the subject, including on the back, on the side, and on the stomach. By utilizing this property, the sleep position of the subject can be determined according to the magnitude relationship that holds for the levels of the extracted respiration signals.

The sleep position determination device may be further provided with a notification device that notifies a user of the determination result in a case where the sleep position of the subject is determined to be a sleep position other than on the back.

According to such a configuration, by notifying the user of the sleep position of the subject, it is possible to prompt the user to take appropriate measures depending on the sleep position. For example, in a nursery, by notifying a childcare worker that an infant is in a sleep position other than on the back, it is possible to prompt the childcare worker to return the infant to a sleep position on the back, which is associated with a lower risk of SIDS.

Also, the at least one contactless sensor may be a Doppler radar.

According to such a configuration, by using a Doppler radar, the subject can be measured consistently, and a sleep position determination device with excellent sleep position determination performance is obtained.

A sleep position determination method according to an aspect of the present disclosure includes receiving, from at least one contactless sensor, a measurement result obtained by measuring a subject using the at least one contactless sensor, extracting a respiration signal of the subject from the measurement result, and referencing reference information related to a level of the respiration signal, determining a sleep position of the subject on a basis of a comparison between the level of the respiration signal of the subject and the reference information, and outputting a determination result of the sleep position.

According such a method, by utilizing the property that the level of the respiration signal is different depending on the sleep position of the subject, it is possible to determine the sleep position of a subject on the basis of a comparison between the level of a respiration signal and reference information. Because the respiration signal is extracted from the measurement result of the subject with a contactless sensor, compared to the case of using a contact sensor, the comfort of the subject is not impaired, and furthermore, the burden imposed on a user because of work such as replacing a pressure-sensitive element due to wear and tear as well as daily disinfection can be reduced. As a result, a sleep position determination method that greatly simplifies work is obtained.

A non-transitory computer-readable recording medium according to an aspect of the present disclosure is a non-transitory computer-readable recording medium storing a program for determining a sleep position that, when executed by the computer, performs a process including receiving, from at least one contactless sensor, a measurement result obtained by measuring a subject using the at least one contactless sensor, extracting a respiration signal of the subject from the measurement result, and referencing reference information related to a level of the respiration signal, determining a sleep position of the subject on a basis of a comparison between the level of the respiration signal of the subject and the reference information, and outputting a determination result of the sleep position.

A program according to an aspect of the present disclosure is a program executable by a computer for determining a sleep position, and causes the computer to execute a process including receiving, from at least one contactless sensor, a measurement result obtained by measuring a subject using the at least one contactless sensor, extracting a respiration signal of the subject from the measurement result, and referencing reference information related to a level of the respiration signal, determining a sleep position of the subject on a basis of a comparison between the level of the respiration signal of the subject and the reference information, and outputting a determination result of the sleep position.

According to such a configuration, a computer can be made to execute a sleep position determination method having advantageous effects similar to those described above.

In the present disclosure, all or part of the circuits, units, devices, members, or sections, or all or part of the function blocks in the block diagrams, may also be executed by one or multiple electronic circuits, including a semiconductor device, a semiconductor integrated circuit (IC), or a large-scale integration (LSI) chip, for example. An LSI chip or IC may be integrated into a single chip, or may be configured by combining multiple chips. For example, function blocks other than memory elements may be integrated into a single chip. Although referred to as an LSI chip or IC herein, such electronic circuits may also be called a system LSI chip, a very large-scale integration (VLSI) chip, or an ultra-large-scale integration (ULSI) chip, depending on the degree of integration. A field-programmable gate array (FPGA) programmed after fabrication of the LSI chip, or a reconfigurable logic device in which interconnection relationships inside the LSI chip may be reconfigured or in which circuit demarcations inside the LSI chip may be set up, may also be used for the same purpose.

Furthermore, the function or operation of all or part of a circuit, unit, device, member, or section may also be executed by software processing. In this case, the software is recorded onto a non-transitory recording medium, such as one or multiple ROM modules, optical discs, or hard disk drives, and when the software is executed by a processor, the function specified by the software is executed by the processor and peripheral devices. A system or device may also be provided with one or multiple non-transitory recording media on which the software is recorded, a processor, and necessary hardware devices, such as an interface, for example.

Hereinafter, technology such as a sleep position determination device according to an aspect of the present disclosure will be described specifically with reference to the drawings.

Note that the embodiments described hereinafter all illustrate specific examples of the present disclosure. Features such as numerical values, shapes, materials, structural elements, layout positions and connection states of structural elements, steps, and the ordering of steps indicated in the following embodiments are merely examples, and are not intended to limit the present disclosure. In addition, among the structural elements in the following embodiments, structural elements that are not described in the independent claim indicating the broadest concept are described as arbitrary or optional structural elements.

Embodiment 1

FIG. 1 is a block diagram illustrating an example of a functional configuration of a sleep position determination device 10. FIG. 1 illustrates the sleep position determination device 10 together with a contactless sensor 70. The contactless sensor 70 may also be included in the sleep position determination device 10.

First, the contactless sensor 70 will be described. The contactless sensor 70 measures, in a non-contacting way, the distance to a subject and the motion of the subject inside a detection area. The contactless sensor 70 includes a Doppler radar, for example. A Doppler radar measures the distance to the subject and the motion of the subject in a non-contacting way by transmitting an ultrasonic wave or an electromagnetic wave as a search wave toward the detection area, and receiving a reflected wave from the subject.

Figures 2, 3:
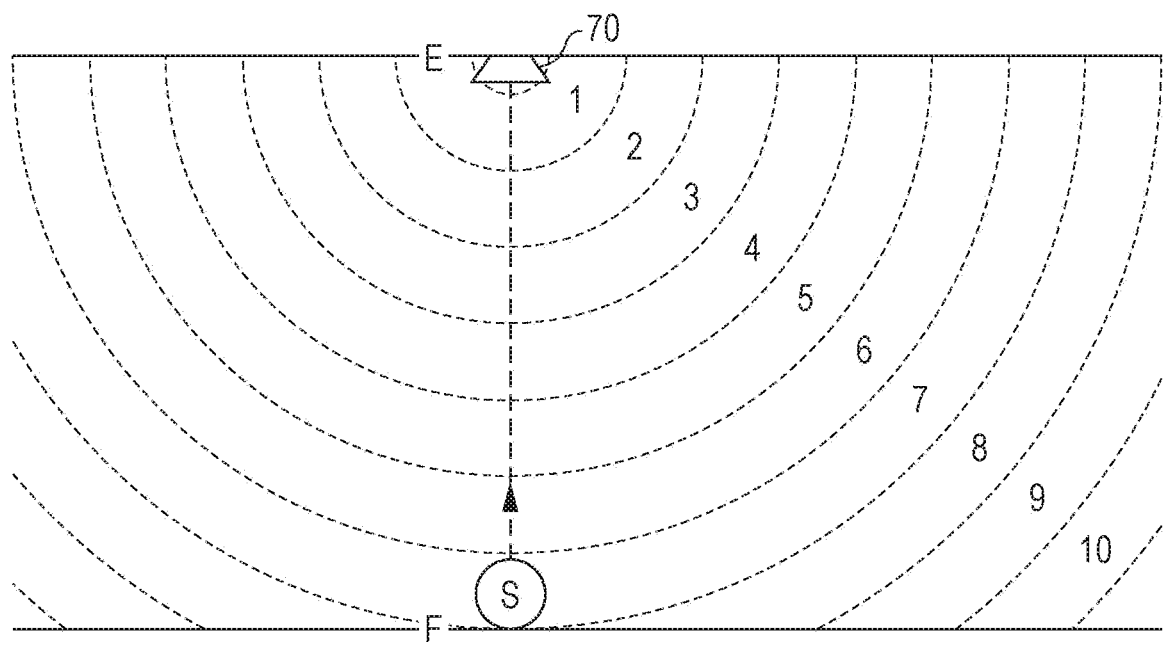
FIG. 2 is a diagram illustrating an example of a measurement result from a contactless sensor according to Embodiment 1.
FIG. 3 is a conceptual diagram for describing an example of measurement conditions according to Embodiment 1.

FIG. 2 is a diagram illustrating an example of a measurement result from the contactless sensor 70. As illustrated in FIG. 2, a measurement result 110 of the contactless sensor 70 includes a reflection intensity 112 and a phase rotation amount 113 for each range bin 111.

The range bins 111 express discrete measurement results of the distance from the contactless sensor 70 to the subject, and correspond to the one-way time from the transmission of a search wave to the reception of a reflected wave. The width of the range bins 111, or in other words the distance resolution, is for example 7.5 centimeters in the case where the search wave is a radio wave in the millimeter-wave band with a pulse width of 0.5 nanoseconds. The reflection intensity 112 is the intensity of the reflected wave, and expresses the certainty that the subject is present in the corresponding range bin. The phase rotation amount 113 is the amount of change in the phase of the reflected wave with respect to the search wave, and the change over time in the phase rotation amount corresponds to the relative velocity of the subject (for example, the body motion due to respiration by the subject). Here, the relative velocity of the subject means the velocity component in the line-of-sight direction pointing from the contactless sensor 70 to the subject.

Referring to FIG. 1, the sleep position determination device 10 is provided with a receiver 11, an extraction circuit 12, memory 13, a determination circuit 14, and a notification device 15.

The receiver 11 receives the measurement result obtained by the contactless sensor 70 measuring the subject inside the detection area. The measurement result may also express the distance to the subject and the motion of the subject. The extraction circuit 12 extracts a respiration signal from the received measurement result. The memory 13 stores reference information related to the level of the respiration signal.

The determination circuit 14 determines the sleep position of the subject on the basis of a comparison between the level of the extracted respiration signal and the reference information, and outputs a determination result. The notification device 15 notifies a user of the determination result in a case where the sleep position of the subject is determined to be a sleep position other than on the back. Here, the user refers to a person such as a childcare worker or a nurse who monitors the state of health of the subject, for example.

The sleep position determination device 10 includes a computer system provided with as a processor, memory, a communication circuit, and the like, for example. The individual components of the sleep position determination device 10 illustrated in FIG. 1 may be software functions achieved by the processor executing a program recorded in the memory, for example.

Next, operations by the sleep position determination device 10 configured as described above will be described on the basis of a specific example of measurement conditions.

FIG. 3 is a conceptual diagram for describing an example of measurement conditions. FIG. 3 schematically illustrates conditions in which the contactless sensor 70 is disposed on a ceiling E, and a subject S is on a floor F. In FIG. 3, the regions between adjacent concentric circles represent the range bins, and the numerals assigned in the radial direction of the concentric circles express the numbers of the range bins. The range bins are three-dimensional regions shaped like concentric circular shells extending in all directions. In FIG. 3, the contactless sensor 70 is illustrated directly above the subject S for simplicity, but the contactless sensor 70 may also be disposed obliquely above the subject S.

Figure 4:
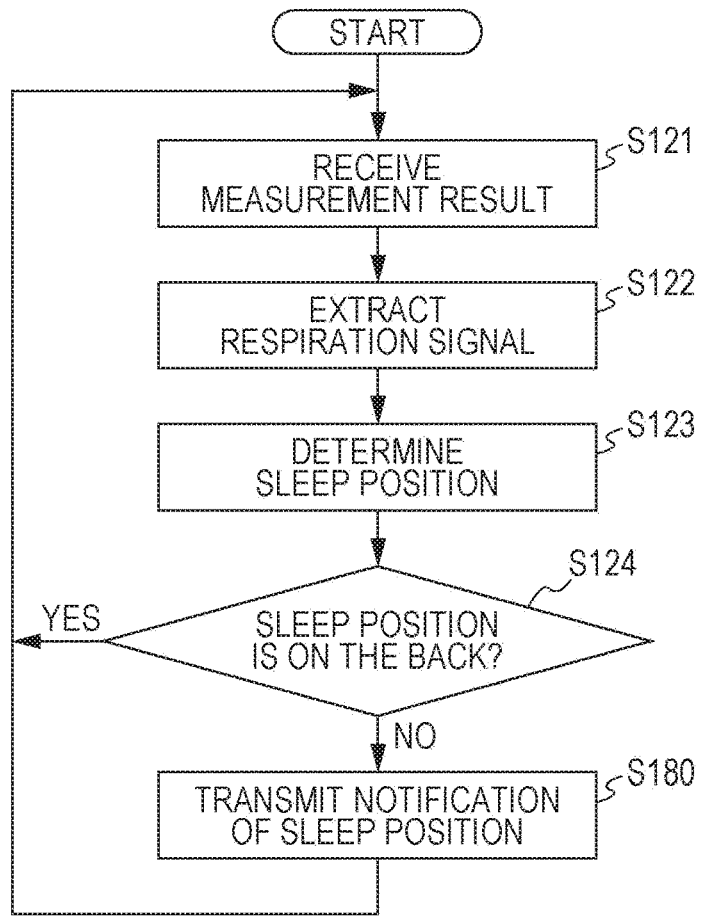
FIG. 4 is a flowchart illustrating an example of operations by the sleep position determination device according to Embodiment 1.

FIG. 4 is a flowchart illustrating an example of operations by the sleep position determination device 10.

In the measurement conditions of FIG. 3, the sleep position determination device 10 operates as follows, in accordance with the flowchart in FIG. 4.

The receiver 11 receives a measurement result from the contactless sensor 70 (S121).

Figure 5:
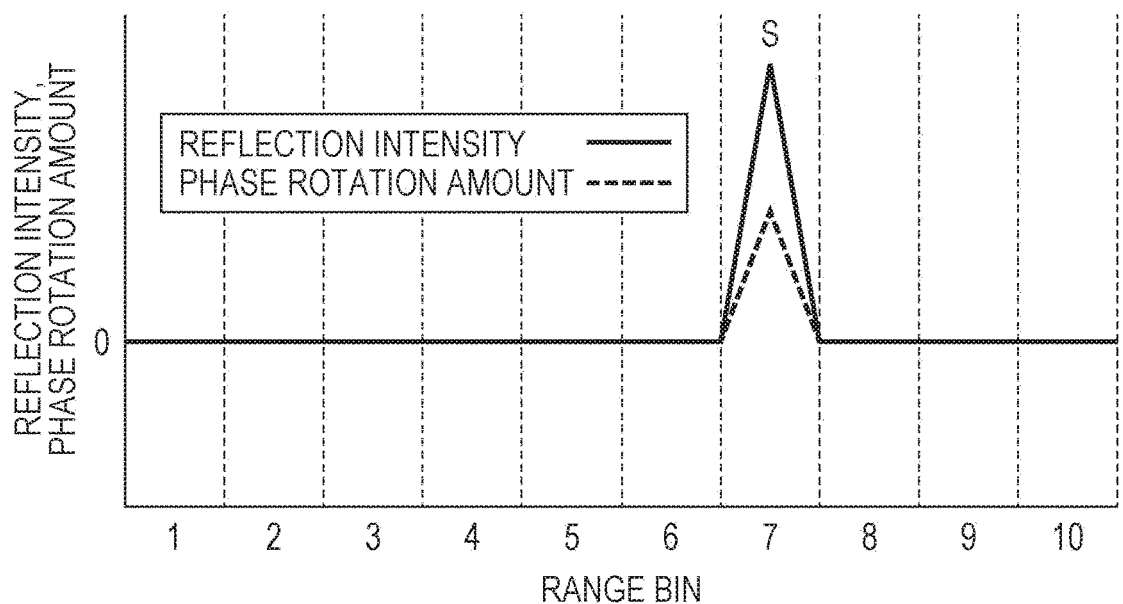
FIG. 5 is a graph illustrating an example of a measurement result according to Embodiment 1.

FIG. 5 is a graph illustrating an example of a measurement result corresponding to the measurement conditions in FIG. 3. In the example of FIG. 5, in the seventh range bin, a reflection intensity due to the reflected wave from the subject S and a phase rotation amount originating from body motion due to the respiration of the subject S are detected.

The extraction circuit 12 extracts a respiration signal from the received measurement result (S122 in FIG. 4). The respiration signal is the frequency component of approximately a dozen Hz originating from the respiration of the subject included in a time series of measurement results. For example, the extraction circuit 12 may use a low-pass filter or a trend removal filter to extract a respiration signal from a time series of the phase rotation amount at the distance where the subject is present (in the example of FIG. 5, the seventh range bin).

Also, if the distance resolution of the contactless sensor 70 is sufficiently high, it is also possible to obtain the displacement of the body surface of the subject from variation in the range bin where the peak in the reflection intensity appears. In this case, the extraction circuit 12 may also extract a time series of the displacement of the body surface of the subject, or in other words the frequency component of approximately a dozen Hz included in the variation of the range bin where the peak in the reflection intensity appears, as the respiration signal. The level of the extract respiration signal is different depending on the sleep position of the subject.

Figure 6A:
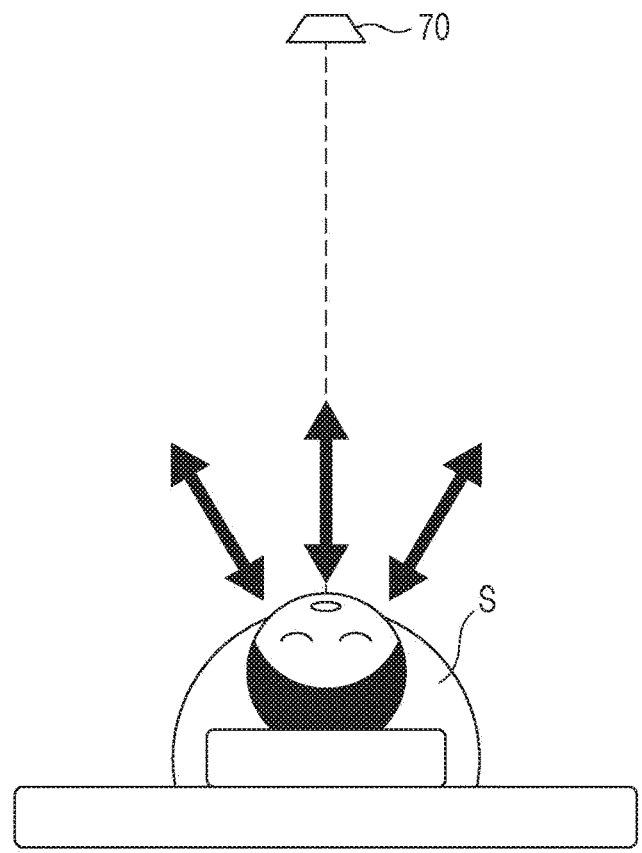
FIG. 6A is a conceptual diagram for describing an example of a sleep position according to Embodiment 1.
Figure 6B:
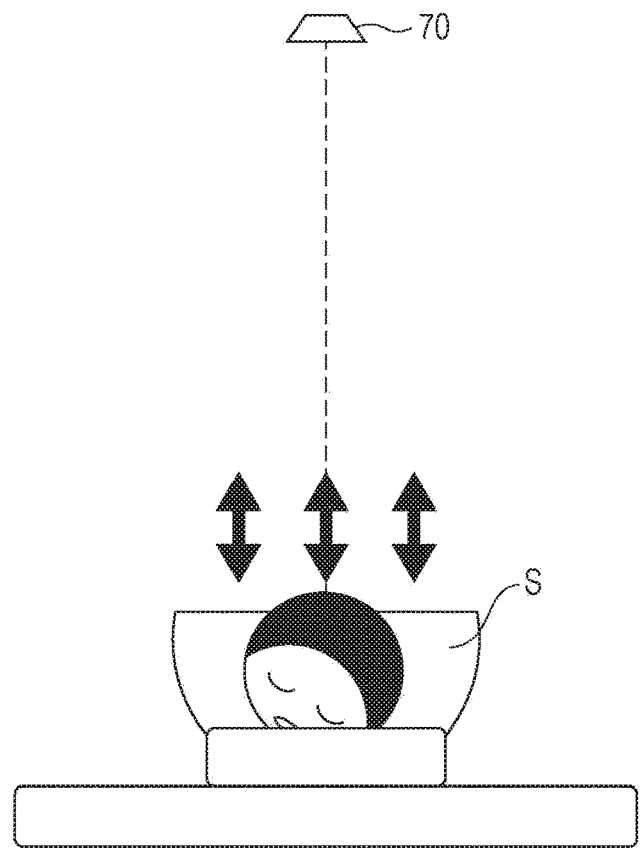
FIG. 6B is a conceptual diagram for describing an example of a sleep position according to Embodiment 1.

FIGS. 6A and 6B are conceptual diagrams for describing respective examples of the sleep position of the subject, in which FIG. 6A illustrates a sleep position on the back, and FIG. 6B illustrates a sleep position on the stomach. As illustrated by the long radial arrows in FIG. 6A, in the sleep position on the back, an expanding and contracting motion occurs radially in the chest and abdomen of the subject S. On the other hand, as illustrated by short parallel arrows in FIG. 6B, in the sleep position on the stomach, a relatively short parallel motion in the vertical direction occurs in the entire back of the subject S.

FIG. 7 is a graph illustrating an example of respiration signals according to sleep positions. FIG. 7 illustrates respiration signals extracted from measurement results by the contactless sensor 70 installed directly above or obliquely above the subject S for the case where the sleep position of the subject is on the back (solid line) and the case where the sleep position of the subject is on the stomach (dashed line).

Because of the differences in the motion of the subject according to the sleep position, a respiration signal of higher level is extracted in the case of the sleep position on the back compared to the case of the sleep position on the stomach. Here, the level of a respiration signal is an appropriate numerical value expressing the magnitude of the respiration signal. As an example, the root mean square over a predetermined length of time (several seconds, for example) of the amplitude of the respiration signal is used as the level of the respiration signal.

In FIG. 7, the levels of the respiration signals of the sleep position on the back and the sleep position on the stomach are labeled L1 and L2, respectively. In the sleep position on the back, among the parts of the body of the subject, the chest and abdomen that move the most in association with respiration are free to move upward, and therefore a respiration signal is having the high level L1 compared to other sleep positions such as on the stomach or on the side not illustrated is extracted.

Consequently, by setting a threshold value TH that is smaller than the level of the respiration signal when the sleep position of the subject is on the back, and comparing the current level of the respiration signal to the threshold value TH, it is possible to determine whether the current sleep position of the subject is on the back or a sleep position other than on the back.

The threshold value TH is not particularly limited, but as an example, the threshold value TH may be set from a measurement result taken before starting sleep position determination. For example, the level of the respiration signal when the sleep position of the subject is on the back may be computed in advance, and a value obtained by multiplying the computed level by a coefficient less than 1 may be treated as the threshold value TH. In addition, the level of the respiration signal in a sleep position on the back and the level of the respiration signal in a sleep position other than on the back may be computed in advance, and an intermediate value between the computed levels may be treated as the threshold value TH.

The set threshold value TH is stored in the memory 13 as the reference information related to the level of the respiration signal.

By referring to the threshold value TH from the memory 13 and comparing the level of the respiration signal extracted from the most recent measurement result to the threshold value TH, the determination circuit 14 determines whether the current sleep position of the subject is on the back or a sleep position other than on the back (S123 in FIG. 4). For example, when the level of the respiration signal is the threshold value TH or higher, the 14 determines that the sleep position of the subject is on the back, whereas when the level of the extracted respiration signal is lower than the threshold value, the determination circuit 14 determines that the sleep position of the subject is other than on the back, and outputs a determination result.

In the case of determining that the sleep position of the subject is on the back (YES in S124), the sleep position determination device 10 continues to determine the sleep position without notifying the user of the sleep position. Note that even if the user is not notified, the determined sleep position may still be saved as a log.

In the case of determining that the sleep position of the subject is other than on the back (NO in S124), the notification device 15 notifies the user of the sleep position (S180). For example, in a nursery, the notification device 15 notifies a childcare worker that an infant is in a sleep position other than on the back through appropriate means such as sound, vibration, and light via a device such as a mobile terminal or a display installed inside the nursery. With this arrangement, the childcare worker can be prompted to return the infant to a sleep position on the back, which is associated with a lower risk of SIDS. Note that the notification by the notification device 15 is not limited to a nursery, and even in a facility such as a hospital or a nursing home for example, a person such as a nurse or an administrator can be notified in a way similar to the above.

In this way, according to the sleep position determination device 10, by utilizing the property that the level of the respiration signal is different depending on the sleep position of the subject, it is possible to determine the sleep position of a subject on the basis of a comparison between the level of a respiration signal and reference information. Because the respiration signal is extracted from the measurement result of the subject with a contactless sensor, compared to the case of using a contact sensor, the comfort of the subject is not impaired, and furthermore, the burden imposed on a user because of work such as replacing a pressure-sensitive element due to wear and tear as well as daily disinfection can be reduced. As a result, a sleep position determination device with excellent ease of use is obtained.

Embodiment 2

Embodiment 2 describes a sleep position determination device that updates the reference information using the respiration signal when the sleep position on the back is determined. Note that components and steps which are the same as the components and steps described in the foregoing embodiment will be referenced by the same signs, and duplicate description will be omitted where appropriate.

Figure 8:
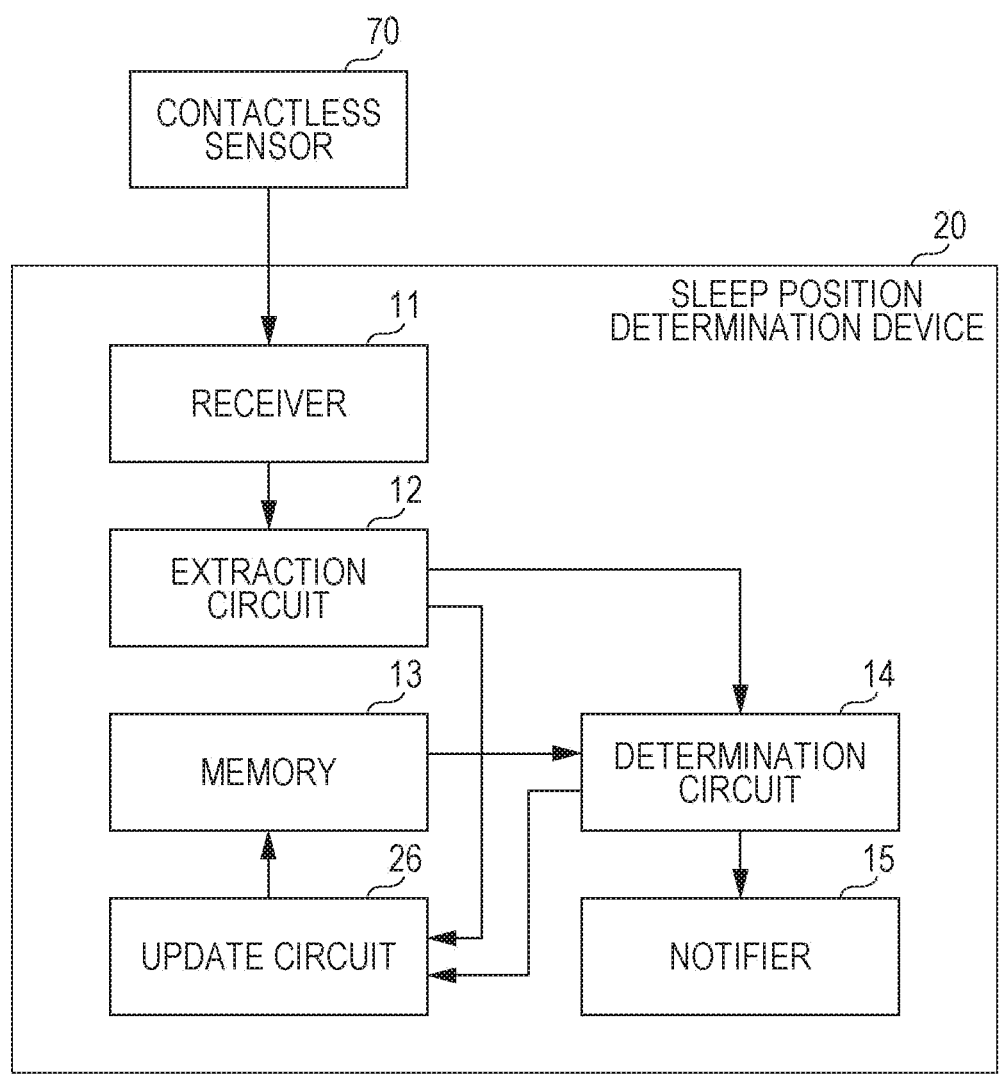
FIG. 8 is a block diagram illustrating an example of a functional configuration of a sleep position determination device according to Embodiment 2.

FIG. 8 is a block diagram illustrating an example of a functional configuration of a sleep position determination device according to Embodiment 2. Compared to the sleep position determination device 10 in FIG. 1, an update circuit 26 is added to the sleep position determination device 20 in FIG. 8.

The update circuit 26 generates new reference information using the respiration signal extracted when the sleep position of the subject is determined to be on the back, and updates the reference information stored in the memory 13 with the new reference information.

Figure 9:
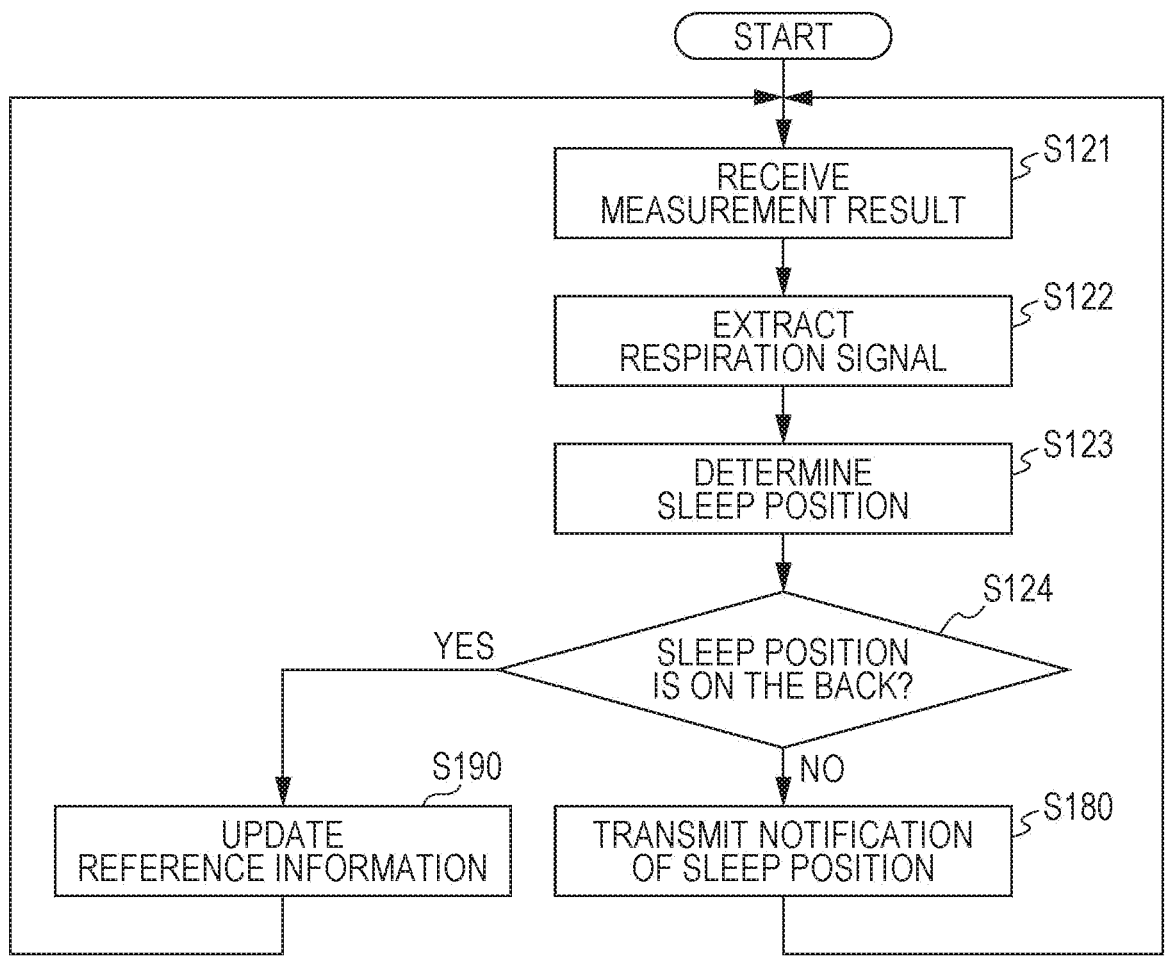
FIG. 9 is a flowchart illustrating an example of operations by the sleep position determination device according to Embodiment 2.

FIG. 9 is a flowchart illustrating an example of operations by the sleep position determination device 20. Compared to the operations by the sleep position determination device 10 in FIG. 4, a step S190 is added to the operations by the sleep position determination device 20 illustrated in FIG. 9.

In the sleep position determination device 20, like the sleep position determination device 10, the sleep position of the subject is determined on the basis of a comparison between the level of the respiration signal and the reference information, and if the sleep position is other than on the back, the user is notified (S121 to S124, S180). The content of steps S110 to S124 and step S180 as well as the applied measurement conditions are the same as those described in Embodiment 1.

In the sleep position determination device 20, when the sleep position of the subject is determined to be on the back (YES in 3124), the level of the respiration signal is collected by the update circuit 26. For example, the update circuit 26 generates a new threshold value by multiplying the average value of the levels of a predetermined number of the most recently collected respiration signals by a coefficient less than 1, and updates the threshold value stored in the memory 13 with the new threshold value, for example.

In this way, according to the sleep position determination device 20, while the determination of the sleep position is performed, the reference information is successively updated by using the respiration signal when the sleep position is determined to be on the back. With this arrangement, because the reference information is updated according to the level of the respiration signal and the time variation of the level specific to the subject, the sleep position of the subject can be determined precisely and consistently according to the individual differences and variations in the physical condition of the subject.

Embodiment 3

The determination of the sleep position may also account for rotational movements by the subject, as typified by rolling over during sleep.

Embodiment 3 describes a sleep position determination device that determines the sleep position of the subject by detecting a rotational movement by the subject, Note that components and steps which are the same as the components and steps described in the foregoing embodiment will be referenced by the same signs, and duplicate description will be omitted where appropriate.

Figure 10:
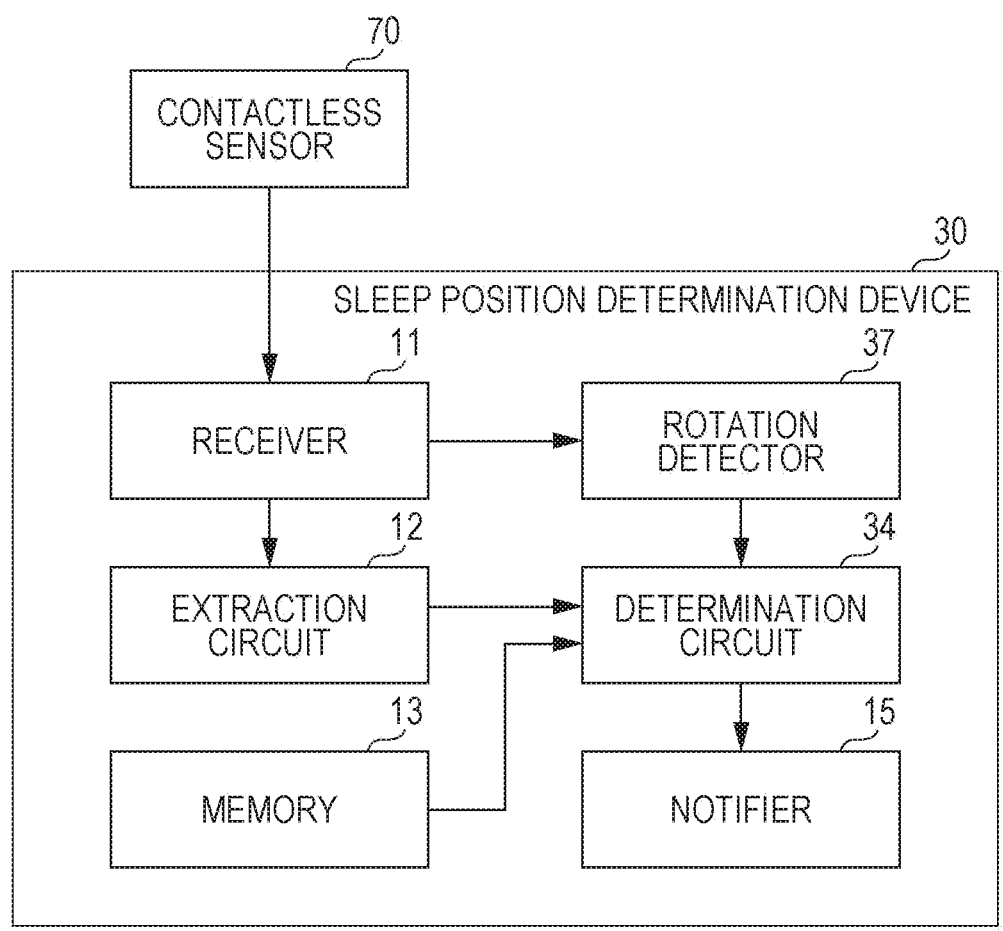
FIG. 10 is a block diagram illustrating an example of a functional configuration of a sleep position determination device according to Embodiment 3.

FIG. 10 is a block diagram illustrating an example of a functional configuration of the sleep position determination device according to Embodiment 3. Compared to the sleep position determination device 10 in FIG. 1, a determination circuit 34 is provided instead of the determination circuit 14 and a rotation detector 37 is added to the sleep position determination device 30 in FIG. 10. The rotation detector 37 detects a rotational movement by the subject from a measurement result.

Figure 11:
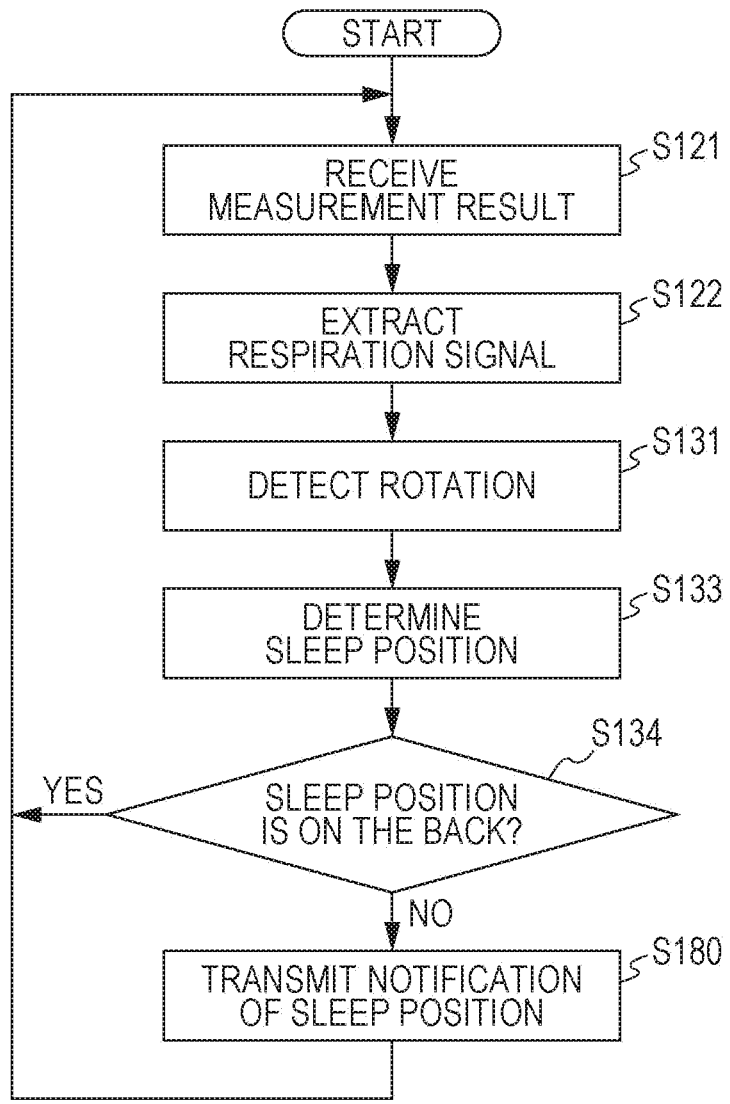
FIG. 11 is a flowchart illustrating an example of operations by the sleep position determination device according to Embodiment 3.

FIG. 11 is a flowchart illustrating an example of operations by the sleep position determination device 30. Compared to the operations by the sleep position determination device 10 in FIG. 4, a step S131 is added and steps S133 and S134 are provided instead of steps S123 and S124 in the operations by the sleep position determination device 30 illustrated in FIG. 11.

In the sleep position determination device 30, like the sleep position determination device 10, a measurement result is received (S121), and a respiration signal is extracted from the measurement result (S122). Additionally, in the sleep position determination device 30, a rotational movement by the subject is detected by the rotation detector 37 (S131).

Figure 12A:
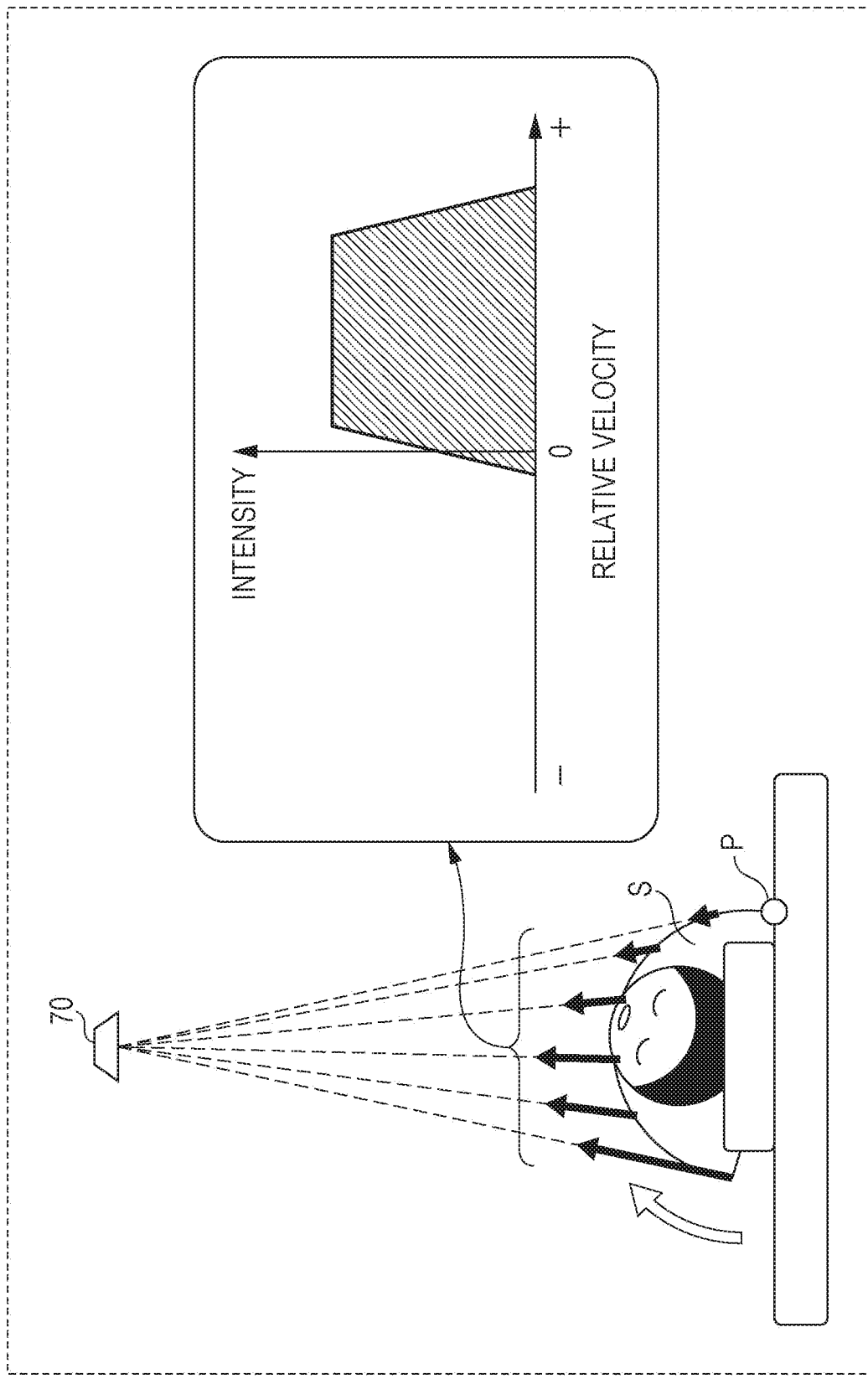
FIG. 12A is a conceptual diagram for describing an example of an approach to rotation detection according to Embodiment 3.
Figure 12B:
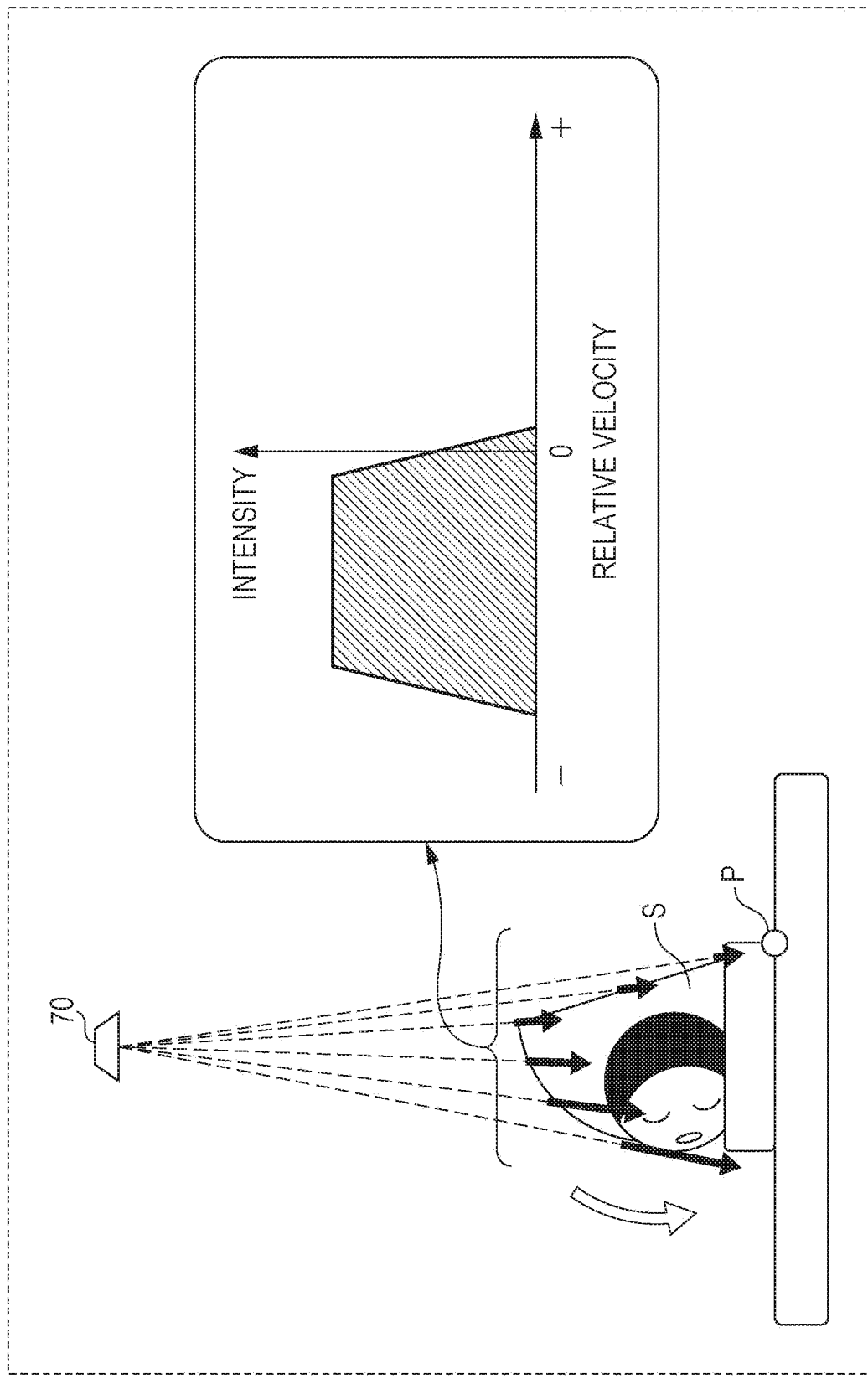
FIG. 12B is a conceptual diagram for describing an example of an approach to rotation detection according to Embodiment 3.

FIGS. 12A and 12B are conceptual diagrams for describing an example of an approach to rotation detection. When the subject S rolls over during sleep as a rotational movement, assume that the subject S attempts to rotate using a part of one side of the body, such as an arm, as a fulcrum point P.

FIG. 12A uses a clockwise white arrow to schematically illustrate a rotational movement for transitioning from a state of sleeping on the back or the stomach to sleeping on the side. In this movement, almost all parts of the body of the subject S move in the direction toward the contactless sensor 70 (the velocity of the movement in this direction is treated as a positive relative velocity), and the relative velocity is also different for each body part, as indicated by the upward-facing black arrows. As a result, a distribution of the relative velocity (hereinafter referred to as a Doppler spectrum) biased positively as illustrated inside the frame on the right is measured.

FIG. 12B uses a counter-clockwise white arrow to schematically illustrate a movement for transitioning from a state of sleeping on the side to sleeping on the stomach or on the back. In this movement, many parts of the body of the subject S move in the direction away from the contactless sensor 70 (the velocity of the movement in this direction is treated as a negative relative velocity), and the relative velocity is also different for each body part, as indicated by the downward-facing black arrows. As a result, a Doppler spectrum biased negatively as illustrated inside the frame on the right is measured.

The Doppler spectrum changes from time to time according to the state of rolling over during sleep. For example, in the case where the subject S changes his or her sleep position from on the back to on the side and then to on the stomach (or the reverse), if observed in a time series, a pattern occurs such that a distribution in which a positive relative velocity is dominant appears, and thereafter, a distribution in which a negative relative velocity is dominant appears.

Accordingly, the rotation detector 37 detects a rotational movement by the subject from the measurement result of the Doppler spectrum.

The determination circuit 34 uses the rotational movement detection result in addition to the comparison between the level of the respiration signal and the reference information to determine the sleep position of the subject (S133 in FIG. 11). For example, in the case where a rotational movement is detected in a state of determining that the sleep position of the subject is on the back, the determination circuit 34 may determine that the sleep position of the subject has become a sleep position other than on the back, even if the level of the respiration signal is the threshold value or higher. In addition, it is possible to distinguish from a change of sleep position and detect a situation in which the subject is at risk of an abnormality, such as a cessation of breathing, in cases such as when the level of the respiration signal is lowered without being associated with a rotational movement.

The notification device 15 notifies the user of a situation in which the subject is at risk of an abnormality, in addition to notifying the user that the subject is in a sleep position other than on the back (S180).

In this way, according to the sleep position determination device 30, because the sleep position of the subject is determined by using the rotational movement detection result in addition to the comparison between the level of the respiration signal and the reference information, the sleep position of the subject can be determined more accurately. As a result, changes in the sleep position and abnormal situations that cannot be detected by a comparison between the level of the respiration signal and the reference information alone can be detected appropriately, and the user can be notified.

Embodiment 4

The contactless sensor used to determine the sleep position of the subject is not limited to a single sensor. A plurality of contactless sensors may also be used to determine the sleep position.

Embodiment 4 describes a sleep position determination device that determines the sleep position of the subject by using measurement results obtained by a plurality of contactless sensors measuring the subject. Note that components and steps which are the same as the components and steps described in the foregoing embodiment will be referenced by the same signs, and duplicate description will be omitted where appropriate.

Figure 13:
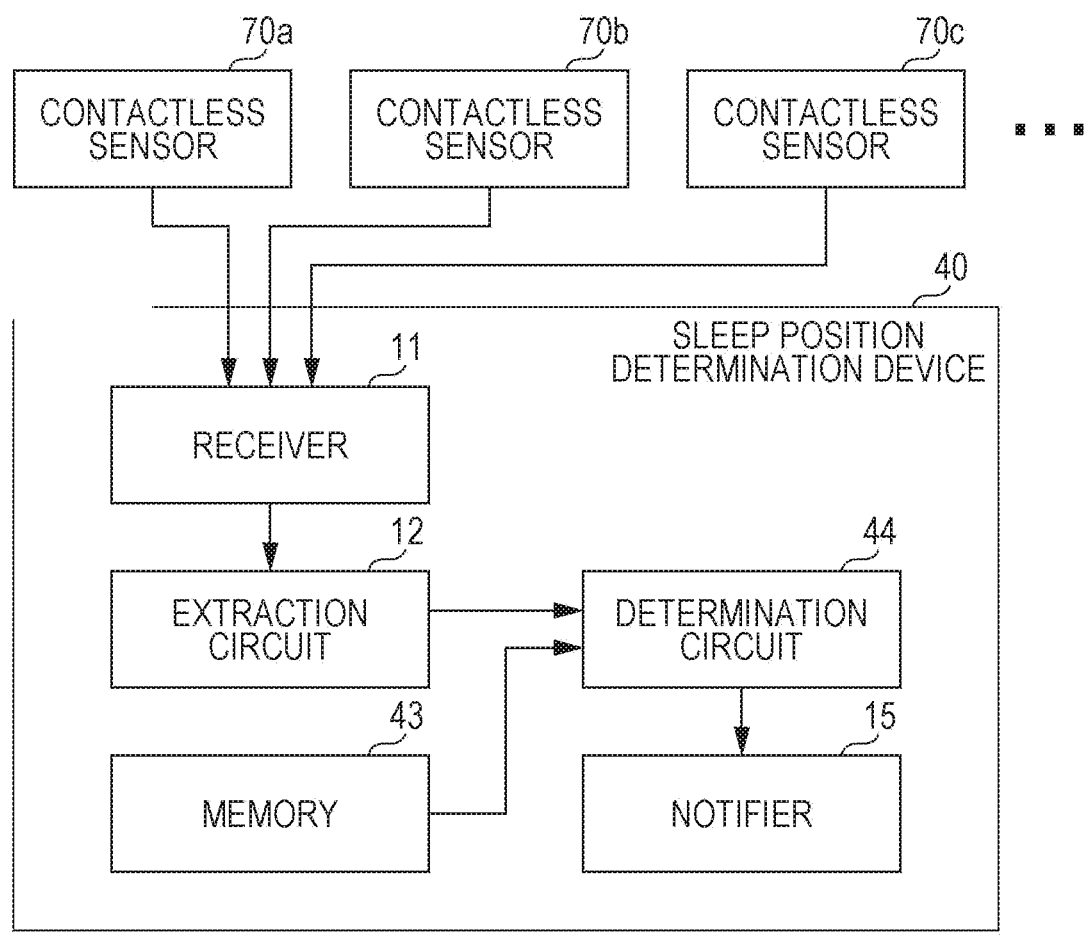
FIG. 13 is a block diagram illustrating an example of a functional configuration of a sleep position determination device according to Embodiment 4.

FIG. 13 is a block diagram illustrating an example of a functional configuration of the sleep position determination device according to Embodiment 4. Compared to the sleep position determination device 10 in FIG. 1, the sleep position determination device 40 in FIG. 13 is provided with memory 43 and a determination circuit 44 instead of the memory 13 and the determination circuit 14. Also, a plurality of contactless sensors 70a, 70b, and 70c provided in mutually different directions with respect to the subject (for example, directly above and obliquely above) are used. The plurality of contactless sensors 70a, 70b, and 70c may also be included in the sleep position determination device 40. The plurality of contactless sensors may also be two sensors, or four or more sensors.

The memory 43 stores reference information related to the relationship among the levels of the respiration signals from the plurality of contactless sensors 70a, 70b, and 70c. The determination circuit 44 determines the sleep position of the subject on the basis of a comparison between the relationship among the levels of the extracted respiration signals from the plurality of contactless sensors 70a, 70b, and 70c and the reference information stored in the memory 43.

Figure 14:
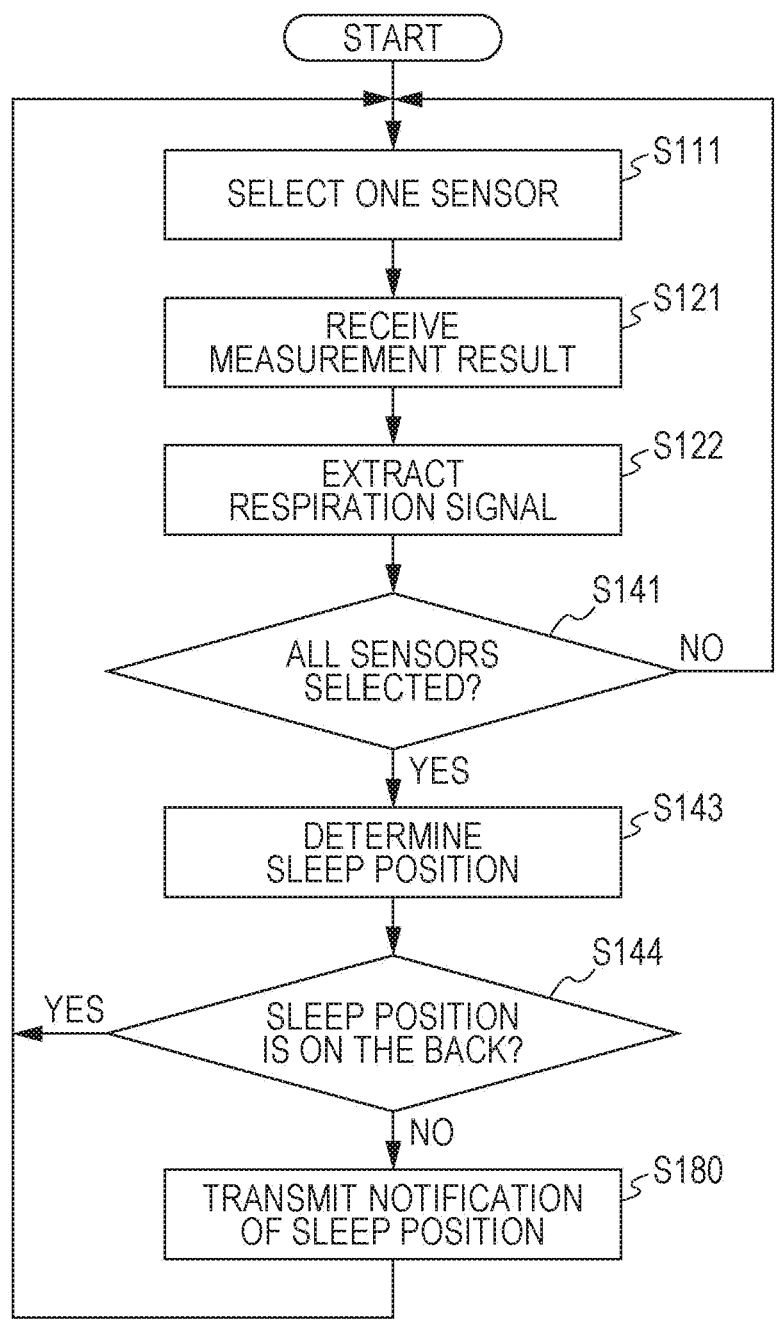
FIG. 14 is a flowchart illustrating an example of operations by the sleep position determination device according to Embodiment 4.

FIG. 14 is a flowchart illustrating an example of operations by the sleep position determination device 40. Compared to the operations by the sleep position determination device 10 in FIG. 4, steps S111 and S141 are added and steps S143 and S144 are provided instead of steps S123 and S124 in the operations by the sleep position determination device 40 illustrated in FIG. 14.

In the sleep position determination device 40, a process of selecting one of the plurality of contactless sensors (S111) and extracting the respiration signal from the measurement result of the selected contactless sensor (S121, S122) is repeated until all contactless sensors have been selected (S141).

When respiration signals are extracted for all contactless sensors (YES in S141), the determination circuit 44 determines the sleep position of the subject on the basis of a comparison between the relationship among the levels of the extracted respiration signals from the plurality of contactless sensors and the reference information.

The relationship among the levels of the extracted respiration signals from the plurality of contactless sensors is different depending on the sleep position of the subject.

FIGS. 15A to 15D are conceptual diagrams for describing examples of the relationship among the levels of a plurality of respiration signals according to the sleep position. FIGS. 15A to 15D illustrate the relationship among the levels La, Lb, and Lc of respiration signals extracted from the measurement results by the plurality of contactless sensors 70a, 70b, and 70c for the cases where the sleep position of the subject S is on the back, on the stomach, on the right side, and on the left side, respectively. The plurality of contactless sensors 70a, 70b, and 70c are installed directly above, obliquely above to the left, and obliquely above to the right of the subject S, respectively.

Figure 15A:
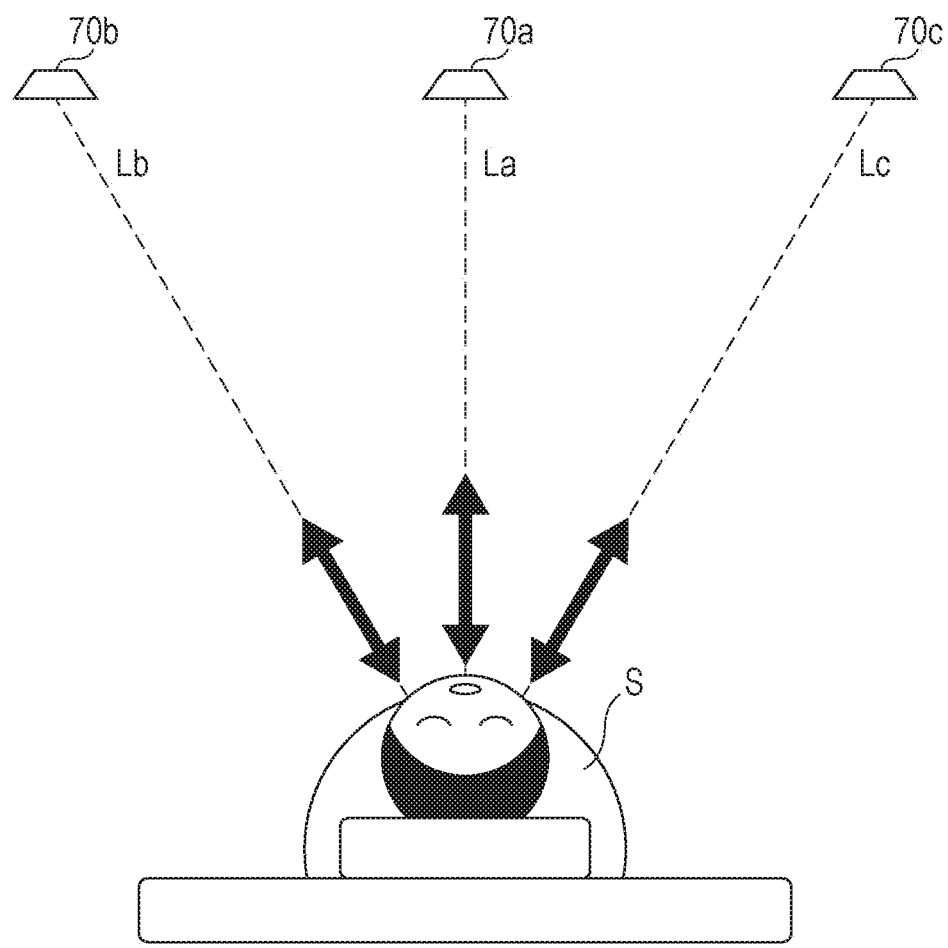
FIG. 15A is a conceptual diagram for describing an example of the relationship among the respiration levels from a plurality of contactless sensors depending on the sleep position according to Embodiment 4.

As FIG. 15A demonstrates, in the sleep position on the back, a radially expanding and contracting motion occurs in the chest and abdomen of the subject S due to respiration. Because the radial motion of the chest and abdomen is isotropic from the perspective of any of the plurality of contactless sensors 70a, 70b, and 70c, the levels La, Lb, and Lc of the respirations signals are substantially the same. In other words, the levels La, Lb, and Lc of the respiration signals exist in the relationship Lb≈La≈Lc.

Figure 15B:
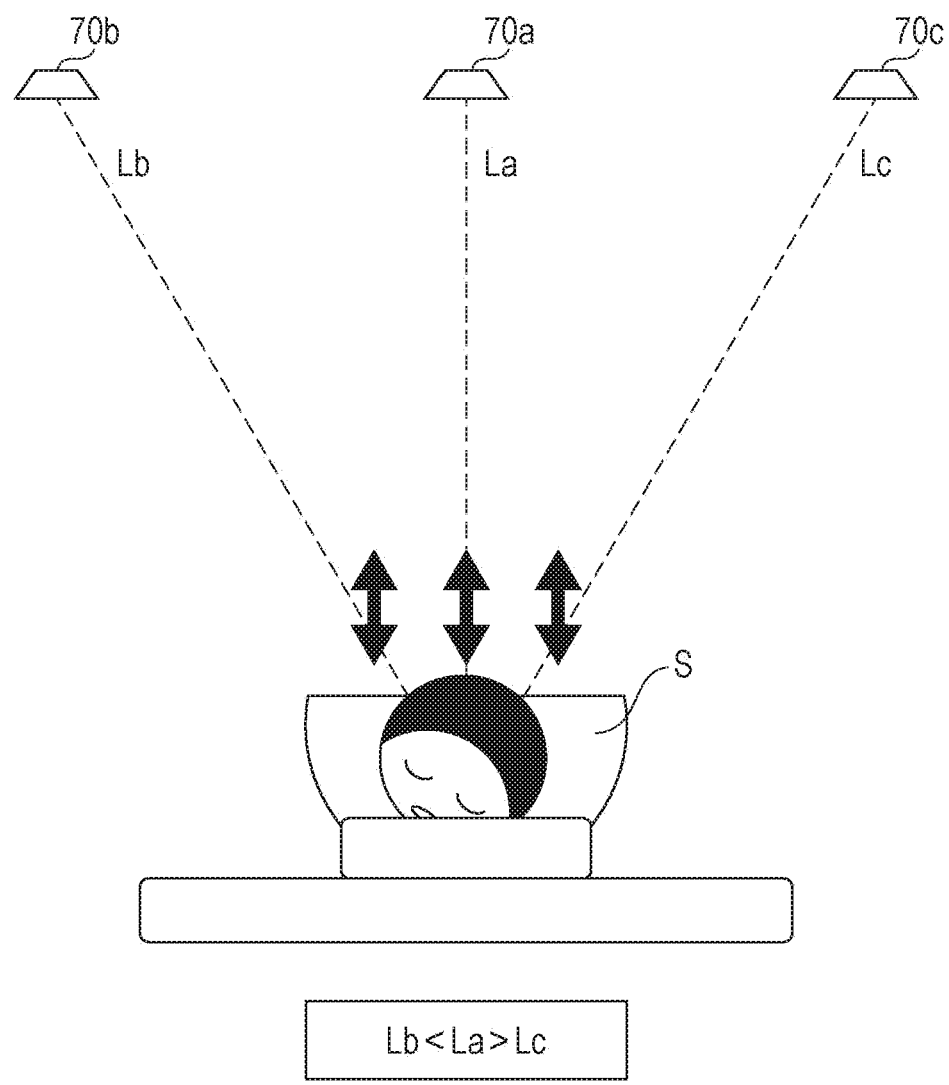
FIG. 15B is a conceptual diagram for describing an example of the relationship among the respiration levels from a plurality of contactless sensors depending on the sleep position according to Embodiment 4.

Also, as FIG. 15B demonstrates, in the sleep position on the stomach, a parallel motion in the vertical direction occurs in the entire back of the subject S due to respiration. Because the motion of the back appears smaller from the oblique perspectives of the contactless sensors 70b and 70c compared to directly above perspective of the contactless sensor 70a, the respiration signal levels Lb and Lc are smaller than the respiration signal level La. In other words, the levels La, Lb, and Lc of the respiration signals exist in the relationship Lb<La>Lc, Also, as FIGS. 15C and 15D demonstrate, in the sleep position on the right side or on the left side, a radially expanding and contracting motion occurs in the chest and abdomen of the subject S due to respiration, while in addition, a horizontal motion occurs in the entire back. The motion of the back of the subject S is smaller than the motion of the chest and abdomen, and the motion on the side of the body is even smaller than the motion of the back.

Figure 15C:
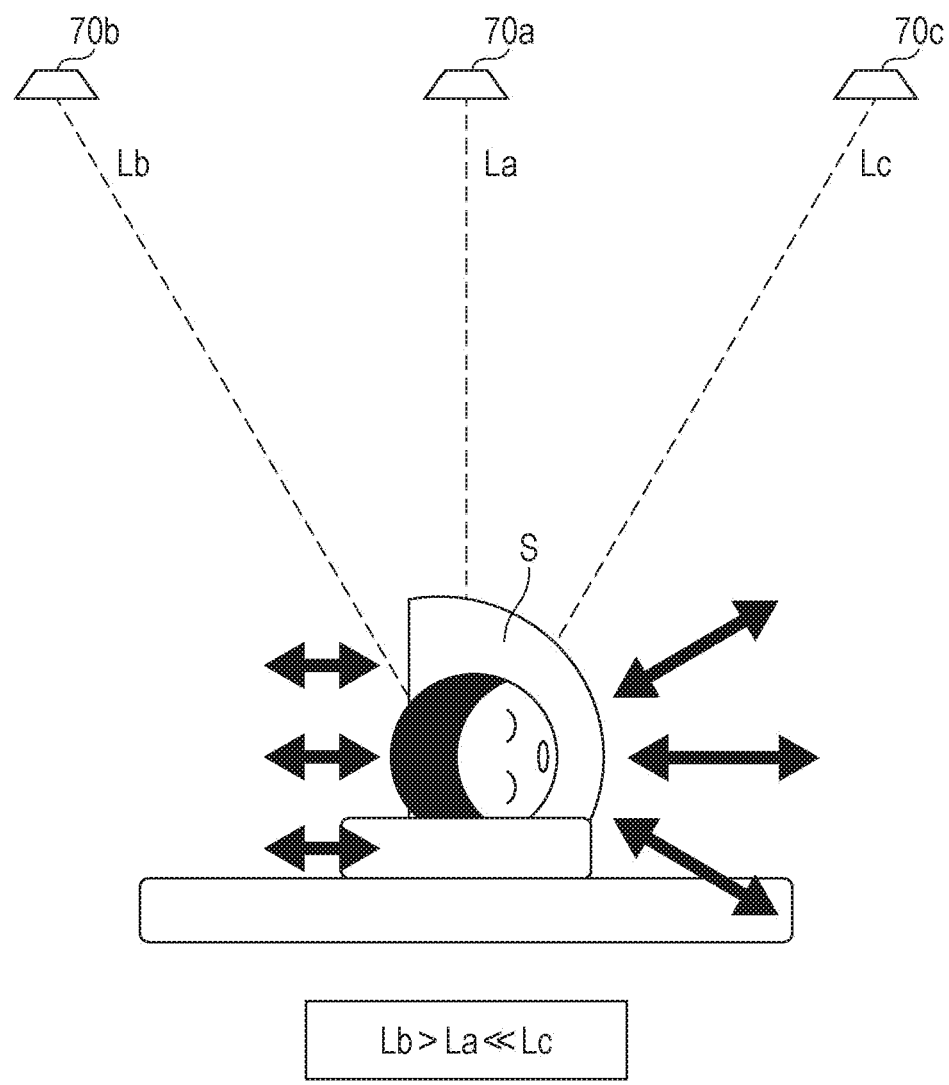
FIG. 15C is a conceptual diagram for describing an example of the relationship among the respiration levels from a plurality of contactless sensors depending on the sleep position according to Embodiment 4.

In the example of FIG. 15C, the contactless sensors 70a, 70b, and 70c measure the side of the body, the back, and the chest and abdomen of the subject S, respectively. For this reason, the level Lc of the respiration signal from the contactless sensor 70c is the largest, followed by the level Lb of the respiration signal from the contactless sensor 70b, and the level La of the respiration signal from the contactless sensor 70a is the smallest. In other words, the levels La, Lb, and Lc of the respiration signals exist in the relationship Lb>La<<Lc.

Figure 15D:
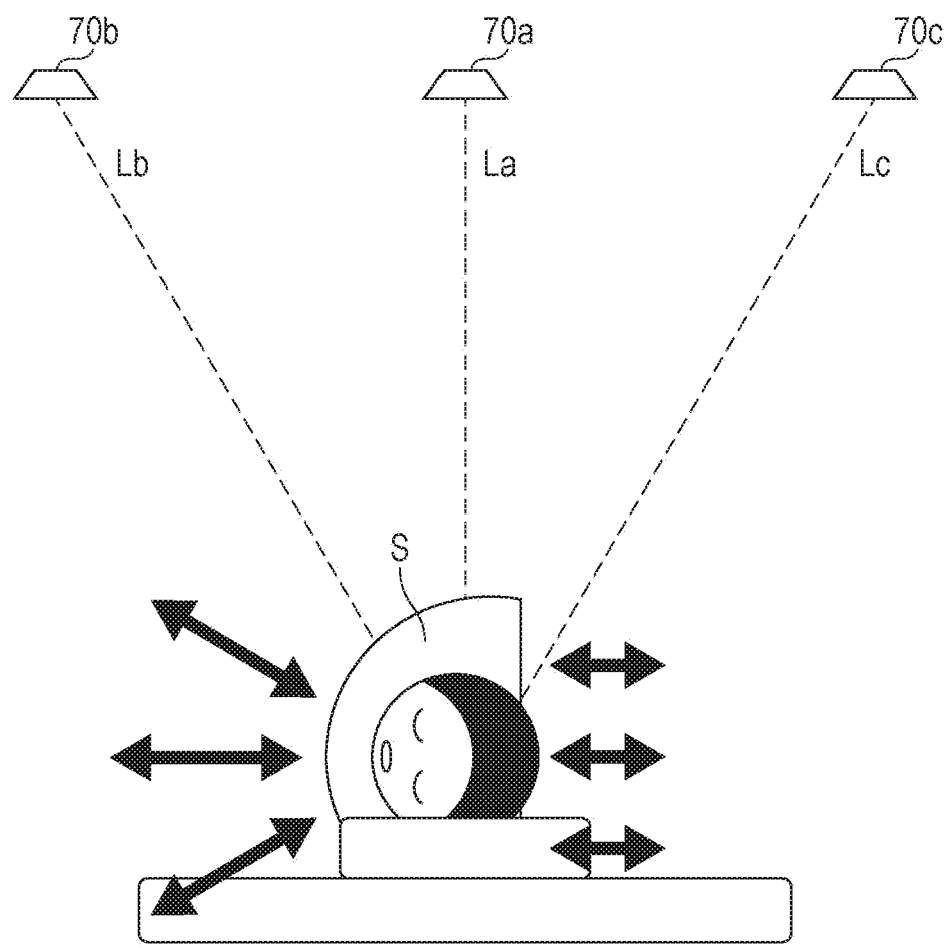
FIG. 15D is a conceptual diagram for describing an example of the relationship among the respiration levels from a plurality of contactless sensors depending on the sleep position according to Embodiment 4.

In the example of FIG. 15D, the contactless sensors 70a, 70b, and 70c measure the side of the body, the chest and abdomen, and the back of the subject S, respectively. For this reason, the level Lb of the respiration signal from the contactless sensor 70b is the largest, followed by the level Lc of the respiration signal from the contactless sensor 70c, and the level La of the respiration signal from the contactless sensor 70a is the smallest. In other words, the levels La, Lb, and Lc of the respiration signals exist in the relationship Lb>>La<Lc.

The relationship among the levels La, Lb, and Lc of the respiration signals illustrated in the examples of FIGS. 15A to 15D is an example of the relationship among the levels of the respiration signals from the contactless sensors.

The memory 43 expresses the relationship among the levels La, Lb, and Lc of the respiration signals according to the relational expressions described above, for example, and stores the relational expressions in association with sleep positions (not illustrated).

The determination circuit 44 determines the sleep position of the subject on the basis of a comparison between the current relationship among the levels La, Lb, and Lc of the respiration signals and the reference information stored in the memory 43. Specifically, the determination circuit 44 determines the sleep position stored in the memory 43 in association with the relational expression that holds true for the current levels La, Lb, and Lc of the respiration signals as the sleep position of the subject.

In this way, according to the sleep position determination device 40, by utilizing the property that the relationship among the levels of the respiration signals from the plurality of contactless sensors is different depending on the sleep position of the subject, it is possible to determine the sleep position of the subject on the basis of a comparison between the relationship among the levels of extracted respiration signals from a plurality of contactless sensors and the reference information. This arrangement makes it possible to determine more types of sleep positions more accurately compared to a simple threshold value comparison.

Note that although all of the embodiments of the present disclosure illustrate an example where the contactless sensor is installed directly above or obliquely above the subject, the configuration is not limited thereto. Signal correction or the like may also be performed as necessary to install the contactless sensor at a position other than directly above or obliquely above the subject, The foregoing describes a sleep position determination device, a sleep position determination method, and a program according to embodiments of the present disclosure, but the present disclosure is not limited to these embodiments. Embodiments obtained by applying various modifications that may occur to persons skilled in the art as well as embodiments constructed by combining the components in different embodiments may also be included within the scope of the one or more exemplary embodiments of the present disclosure, insofar as such embodiments do not depart from the gist of the present disclosure.

The sleep position determination device, sleep position determination method, and non-transitory computer-readable recording medium of the present disclosure can be used broadly in applications that determine sleep position, such as an infant monitoring system in a nursery or other facility, for example.

What is claimed is:

1. A sleep position determination system comprising:
a contactless sensor that includes a transmitter transmitting an ultrasonic wave or an electromagnetic wave to a subject;
a receiver that receives a measurement result obtained by detecting a reflected wave from the subject;
an extraction circuit that extracts a respiration signal of the subject from the measurement result by transforming a time variation of a signal representing the reflected wave to the respiration signal;
a memory that stores first reference information related to a level of the respiration signal;
a rotation detector that detects a presence or absence of a rotational movement comprising a rolling motion of a body of the subject from the measurement result by monitoring the time variation of the signal representing the reflected wave; and
a processor that determines a sleep position of the subject on a basis of a first comparison between the level of the respiration signal of the subject and the first reference information,
wherein the processor determines that an abnormality of the subject is suspected when both of the following conditions are met: (i) the level of the respiration signal of the subject has decreased, and (ii) the decrease in the level of the respiration signal of the subject has occurred without simultaneously detecting the rolling motion of the body.

2. The sleep position determination system according to claim 1, wherein the extraction circuit extracts a periodic body motion of the subject expressed by the measurement result as the respiration signal.

3. The sleep position determination system according to claim 1, wherein
the first reference information is a threshold value of the level of the respiration signal,
in a case where the level of the respiration signal of the subject is equal to or greater than the threshold value, the processor determines that the sleep position of the subject is on the back, and
in a case where the level of the respiration signal of the subject is less than the threshold value, the processor determines that the sleep position of the subject is other than on the back.

4. The sleep position determination system according to claim 3, further comprising: an update circuit that generates new first reference information using the respiration signal of the subject extracted in a case where the sleep position of the subject is determined to be on the back, and updates the first reference information stored in the memory with the new first reference information.

5. The sleep position determination system according to claim 1, further comprising:
the rotation detector that detects the rotational movement of the subject from the measurement result, wherein
the processor determines the sleep position of the subject on a basis of the first comparison and a detection result of the rotational movement.

6. The sleep position determination system according to claim 1, wherein
the at least one contactless sensor includes a plurality of contactless sensors,
the plurality of contactless sensors are provided in mutually different directions with respect to the subject,
the receiver receives the measurement result from each of the plurality of contactless sensors,
the extraction circuit extracts a respiration signal of the subject from the measurement result for each of the plurality of contactless sensors,
the memory additionally stores second reference information related to a relationship among levels of the respiration signals from the plurality of contactless sensors, and
the processor determines the sleep position of the subject on a basis of a second comparison between the relationship among the levels of the respiration signals of the subject from the plurality of contactless sensors and the second reference information.

7. The sleep position determination system according to claim 6, wherein
the second reference information expresses a relationship among the levels of the respiration signals from the plurality of contactless sensors in correspondence with each of a plurality of sleep positions including on the back, on the side, and on the stomach, and
the processor determines which among the plurality of sleep positions is the sleep position of the subject on the basis of the second comparison.

8. The sleep position determination system according to claim 1, further comprising:
a notification device that notifies a user of the determination result in a case where the sleep position of the subject is determined to be a sleep position other than on the back.

9. The sleep position determination system according to claim 1, wherein the at least one contactless sensor is a Doppler radar.

10. A sleep position determination method comprising:
causing a contactless sensor including a transmitter to transmit an ultrasonic wave or an electromagnetic wave to a subject;
receiving a measurement result obtained by detecting a reflected wave from the subject;
extracting a respiration signal of the subject from the measurement result by transforming a time variation of a signal representing the reflected wave to the respiration signal;
detecting a presence or absence of a rolling motion of a rotational movement comprising a body of the subject from the measurement result by monitoring the time variation of the signal representing the reflected wave;
referencing reference information related to a level of the respiration signal and determining a sleep position of the subject on a basis of a comparison between the level of the respiration signal of the subject and the reference information; and
determining that an abnormality of the subject is suspected when both of the following conditions are met: (i) the level of the respiration signal of the subject has decreased, and (ii) the decrease in the level of the respiration signal of the subject has occurred without simultaneously detecting the rolling motion of the body.

11. A non-transitory computer-readable recording medium storing a program for determining a sleep position that, when executed by a computer, performs a process, the process comprising:
transmitting an ultrasonic wave or an electromagnetic wave to a subject by a transmitter of a contactless sensor;
receiving a measurement result obtained by detecting a reflected wave from the subject;
extracting a respiration signal of the subject from the measurement result by transforming a time variation of a signal representing the reflected wave to the respiration signal;
detecting by a rotation detector a presence or absence of a rotational movement comprising a rolling motion of a body of the subject from the measurement result by monitoring the time variation of the signal representing the reflected wave;
referencing reference information related to a level of the respiration signal and determining a sleep position of the subject on a basis of a comparison between the level of the respiration signal of the subject and the reference information; and
determining that an abnormality of the subject is suspected when both of the following conditions are met: (i) the level of the respiration signal of the subject has decreased, and (ii) the decrease in the level of the respiration signal of the subject has occurred without simultaneously detecting the rolling motion of the body.

* * * * *